United States Patent [19]

Dutcher et al.

[11] Patent Number: 5,040,545

[45] Date of Patent: Aug. 20, 1991

[54] RELEASABLE LOCK ASSEMBLY

[75] Inventors: Robert G. Dutcher; John C. Hill, both of Minneapolis, Minn.

[73] Assignee: Possis Medical, Inc., Minneapolis, Minn.

[21] Appl. No.: 600,627

[22] Filed: Oct. 22, 1990

Related U.S. Application Data

[62] Division of Ser. No. 430,596, Nov. 2, 1989, Pat. No. 4,972,847.

[51] Int. Cl.$^5$ .............................................. A61N 1/00
[52] U.S. Cl. .................................. 128/785; 128/786; 70/19
[58] Field of Search .............. 70/19; 30/233; 128/785, 128/786

[56] References Cited

U.S. PATENT DOCUMENTS

| | | | |
|---|---|---|---|
| 1,066,925 | 7/1913 | Lancaster | 30/233 |
| 4,598,561 | 7/1986 | Girard | 70/19 |
| 4,685,314 | 8/1987 | Greenwalt et al. | 70/19 |
| 4,912,949 | 4/1990 | Bowers | 70/19 |
| 4,943,289 | 7/1990 | Goode et al. | 128/785 |

Primary Examiner—Francis Jaworski
Assistant Examiner—George Manuel
Attorney, Agent, or Firm—Burd, Bartz & Gutenkauf

[57] ABSTRACT

A tool for implanting a pacing lead into heart tissue has a pair of side-by-side beams pivoted together at the opposite ends thereof. The beams have jaws that grip a lead head supporting a helical electrode and a groove for accommodating a section of the lead extended from the head. A releasable lock interposed between the beams operates to hold the beams in jaw closed position to grip the head of the electrode. the lock has flexible fingers and a movable sleeve that allows one hand operation to selectively lock and release of the jaws. The helical electrode has an external layer of platinum black particles resulting in decreased electrical losses at the electrode-tissue interface, increased current density, lower stimulation thresholds, and increased amplitude of sensed electrical signals from the heart tissue.

9 Claims, 4 Drawing Sheets

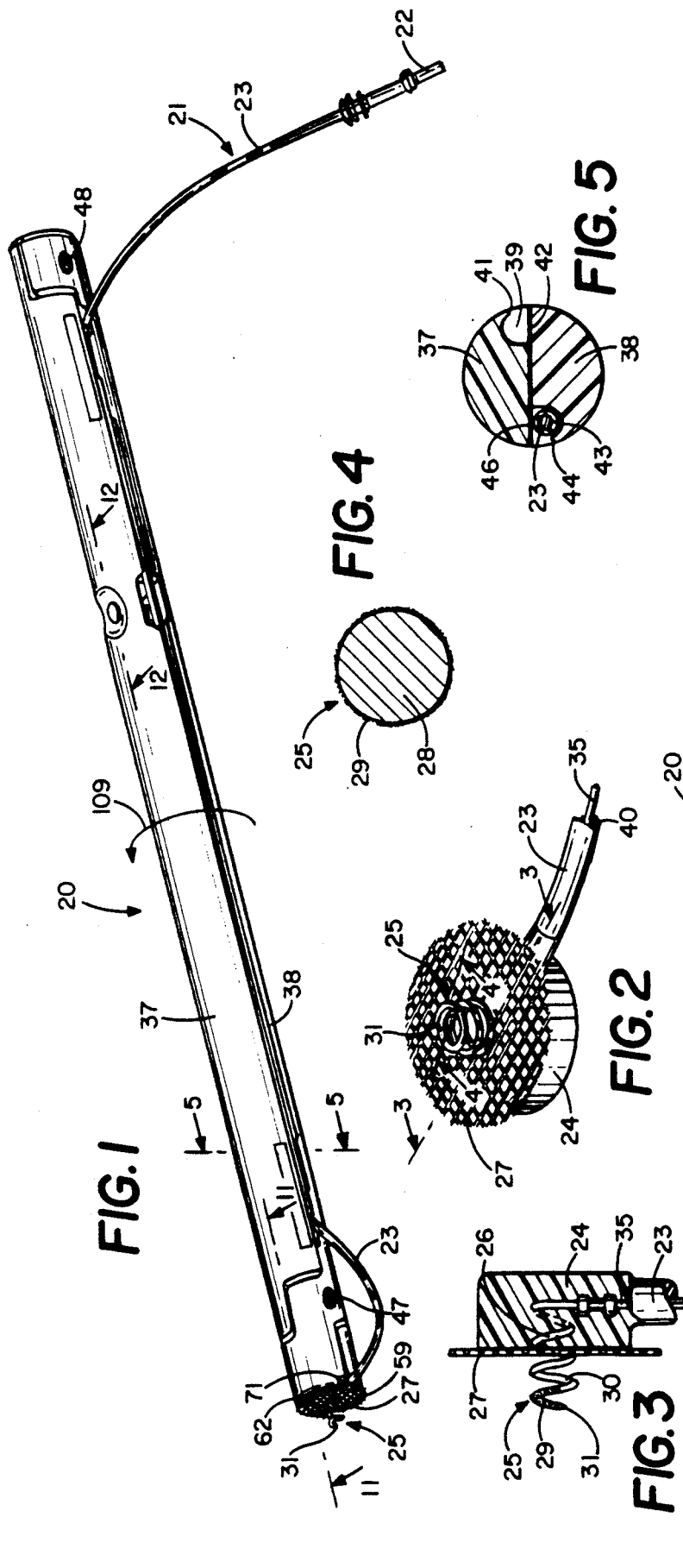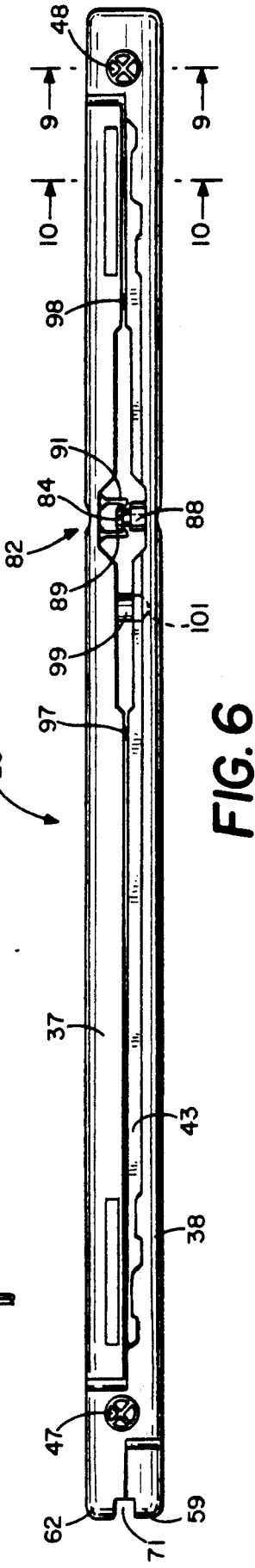

RELEASABLE LOCK ASSEMBLY

This application is a division of application Ser. No. 430,596 filed Nov. 2, 1989, now U.S. Pat. No. 4,972,847.

FIELD OF INVENTION

The invention relates to a field of cardiac pacing leads and an improved hand tool for implanting the lead into myocardial tissue.

BACKGROUND OF THE INVENTION

Hand manipulated tools have been used to screw electrodes into body tissue. Myocardial leads comprising rigid helical coils are turned into heart tissue with elongated rod type tools. An example of this type of tool is disclosed in U.S. Pat. No. 3,737,579 granted to L. R. Bolduc on June 5, 1973. The tool comprises an elongated cylindrical device for holding a lead having a screw type electrode. The head of the lead is force fitted into a slot in the distal end of the tool. A separate rod is used to separate the tool from the lead. Two hands are required to release the lead. U.S. Pat. No. 3,875,947 granted to J. L. Jula and D. Zeidler on Apr. 8, 1975 discloses an elongated generally cylindrical tool for carrying a screw type electrode at its forward end. A portion of the lead fits into an elongated linear slot and one side of the tool. A linearly moveable probe fits into a central passage of the tool to remove the lead from the slot and separate the head from the distal end of the tool after implantation of the lead. This tool requires two handed manipulation to separate the lead from the tool. U.S. Pat. No. 4,271,846 granted to R. L. Little on June 9, 1981 discloses a tool for installing a screw type electrode into body tissue that includes a clamp for holding the lead head on the proximal end of the tool and an elongated rotatable member for releasing the clamp and the lead from the tool. This manipulation procedure also requires the use of two hands.

SUMMARY OF THE INVENTION

The invention is directed to a hand tool or introducer for attaching a screw type pacing lead to the myocardium of a heart. The introducer allows quick one handed release of the entire lead after attachment and fast regrasping, reloading and repositioning of the lead.

The tool has elongated beams that are pivotally connected adjacent their opposite ends. The distal ends of the beams have jaws that grip the head of a pacing lead and hold the electrode mounted on the head in a position for attachment to heart tissue. The beams are moved from an open or bowed position to a closed side-by-side position which moves the jaws into gripping relation with the head. When the beams are in the open position the jaws release the head so that the tool can be removed from the pacing lead without applying twisting or linear forces to the tool. A releasable latch or lock assembly holds the beams in the closed position. The latch assembly is operable in response to movement of the beams toward each other to lock the beams in the closed position so that the jaws firmly grip the head of the pacing lead. This is accomplished with one hand of the operator squeezing adjacent sections of the beams together until the latch assembly locks. The beams are also moved further together with one hand of the operator to release the latch assembly to allow the beams to spread apart and open the jaws.

The preferred embodiment of the tool has elongated beams having semi-cylindrical outer surfaces so that the over-all shape of the tool is generally cylindrical to facilitate one hand manipulation of the tool. Each beam has a longitudinal groove adapted to accommodate a section of the electrical conductor of the lead extending from the head. Lips on the beams extend along the outsides of the grooves to hold the conductor in the grooves. Pivot projections on opposite ends of one beam fit into holes in the other beam to pivotally connect adjacent opposite ends of the beam for limited pivotal movement about generally parallel transverse axes. A biasing spring located between the beams urges the beams to move away from each other to the open bowed position thereby opening semi-circular jaws joined to the distal ends of the beams. The jaws grip opposite sides of the head when the beams are moved to the closed side-by-side position. Adjacent ends of the jaws are spaced from each other to accommodate the conductor end joined to the head. A releasable latch assembly having flexible fingers joined to one beam and a holder on the other beam engagable with the fingers retains the beams in the closed position and jaws gripping the head. A movable sleeve associated with the holder is engaged by the fingers to release the fingers from the holder upon further squeezing the beams toward each other. The locking and releasing of the latch is a one hand operation that does not subject the tool to twisting and linear or longitudinal forces. The electrode implanted in the heart tissue is not disturbed by releasing the jaws from the head and regripping the head with the jaws.

Another feature of the invention is the cardiac pacing lead connectable to a pacemaker for transmitting electric current to heart tissue. The lead has an elongated flexible conductor wire and a sheath of non-electrical conductive material surrounding said conductor wire. An electrical connector attached to the wire is adapted to be connected to a pacemaker. A head of non-electrical conductive material connected to said conductor wire and sheath, support an electrode, such as a rigid helical wire. The helical wire has a portion located externally of said head adapted to be turned into heart tissue to secure the lead to the heart muscle and to transmit pacemaking electrical signals thereto. The helical wire has a sheath of non-electrical conductive material surrounding the wire except for the distal one half turn thereof which represents the electrode. The external portion of the electrode has an outer surface covered with a layer of platinum black particles. The layer of platinum black particles has substantially uniform particles size and uniform distribution on the outer surface whereby said layer of platinum black particles has a uniform microporous outer surface being in surface contact with the heart tissue to decrease electrical losses at the electrode-tissue interface, increase the current density to said heart tissue, establish intimate contact between the electrode and myocardium tissue, lower stimulation thresholds, and increase amplitude of electrical signals from the myocardium.

DESCRIPTION OF DRAWING

FIG. 1 is a perspective view of the introducer of the invention accommodating a myocardial lead;

FIG. 2 is an enlarged perspective view of a myocardial lead such as seen in FIG. 1 separated from the introducer;

FIG. 3 is an enlarged sectional view taken along the line 3—3 of FIG. 2;

FIG. 4 is an enlarged sectional view taken along line 4—4 of FIG. 2;

FIG. 5 is an enlarged sectional view taken along line 5—5 of FIG. 1;

FIG. 6 is an enlarged side elevational view of the introducer in the closed position without the lead;

DESCRIPTION OF PREFERRED EMBODIMENT

Figure 8:
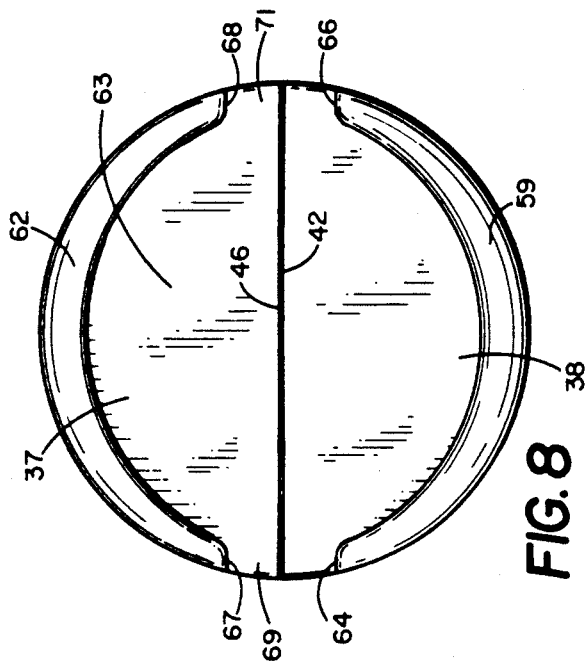
FIG. 8 is an enlarged end view of the distal end of the introducer of FIG. 6.

Referring to FIG. 1, there is shown the myocardial lead installation tool of the invention, known as an introducer, indicated generally at 20 holding a cardiac lead indicated generally at 21 prior to the implantation of the electrode of the lead into the myocardium of a heart. Introducer 20 is disclosed in U.S. application Ser. No. 430,596, incorporated herein by reference. Lead 21 has a connector 22 at the proximal end thereof adapted to be connected to terminal of a pacemaker that generates heart pacing currents. Connector 22 is joined to an elongated flexible electrical conductor 23 having a distal end joined to a generally cylindrical head 24. Head 24 is made of non-electrical conductive material that is biocompatible, such as medical grade silicone rubber. A rigid helical electrode 25 having several convolutions is mounted on the center of head 24. As shown in FIG. 3, electrode 25 has an end 26 embedded in head 24 and connected to conductor wire 35 of conductor 23. Wire 35 is a multifilar conductor coil made of nickel cobalt wire or other suitable conducting material. Wire 35 is enclosed within a non-conductive sheath 40 that is biocompatible, such as medical grade silicone rubber. A generally flat circular netting 27 surrounds electrode 25. Netting 27 is joined to head 24 by bonding it directly to the plastic material of head 24 or suitable connecting materials. The outer peripherial edge of netting 27 projects radially outward from head 24 to increase the surface engagement with the heart tissue. Netting 27 can be porous polyester fiber that enhances fibrotic growth to insure a secure connection of electrode 26 to the heart tissue.

Helical electrode 25 is a rigid helical wire 28 terminating in a pointed end 31. A sheath 30 of non-electrical conductive material, such as medical grade silicone rubber, covers wire 28 except for about the end one half turn section thereof, such as between 160 to 190 degrees of the end section of wire 28. This section of wire 28 comprises the active electrode. Wire 28 can be made of a platinum/irridium. The entire exposed exterior surface of the end one half turn section of wire 28 is completely covered with a coat or layer of platinum black particles to substantially reduce electrode polarization. Wire 28 is platinized to develop the coating of platinum black particles 29. The platinum black is a micro porous surface of submicron size particles. The platinum black particles 29 are electrochemically plated onto the outer surface of the wire or substrate 28. The exterior end portion of wire 28 is placed in a platinum ion plating solution and subjected to an electric d.c. current. The plating solution and wire 28 are also subjected to intermittent ultrasonic vibrations that agitate the platinum ions. The electric current is terminated during the vibration period. The time period between vibration episodes can be varied. An oscillating piezoelectric ceramic is used to generate vibrations at a selected frequency that produces uniform particle size and particle distribution. The submicron size particles of platinum black are bonded to the entire outside surface of wire 28 up to head 24 as seen in FIG. 3. The platinum black particles 29 have substantially uniform particle size and particle distribution resulting in uniform current distribution over the layer of platinum black particles 29 and lower stimulation thresholds. The current carried by lead 21 is delivered to the heart muscle electrolyte almost exclusively through the platinum black particles 29. As shown in FIG. 3 and 4, the layer of platinum black particles 29 has a continuous microporous surface which provides for intimate contact between the end section of electrode 25 and the myocardial tissue and an increase in real surface area with a resulting decrease in electrode-tissue interface electrical losses and an increase the current density to the stimulatable tissue of the heart and thereby lower stimulation thresholds and higher intracardiac electrical signal sensing.

Referring to FIG. 6, introducer 20 comprises a pair of side-by-side elongated beams 37 and 38 having adjacent opposite end sections pivotally connected together with transverse pivot assemblies 47 and 48. The outer surfaces of beams 37 and 38 have generally semi-cylindrical shapes. When introducer 20 is in its closed position, as shown in FIG. 6, beams 37 and 38 have a generally over all elongated cylindrical configuration so that introducer 20 can be operated and manipulated with the fingers of one hand of the operator.

Referring to FIG. 5, beam 37 has a longitudinal side groove 39 open along one side of introducer 20. A longitudinal lip 41 partially closing groove 39 retains a section of conductor 23 in groove 39. Beam 38 has a side groove 43 open along the other side of introducer 20. A portion of the electrical conductor 23 fits into groove 43 and is retained therein by a short lip 44 along one edge of beam 38. Beam 38 has a generally flat transverse face 42 facing groove 39 and a longitudinal groove 43 with an outside lip 44 opposite a transverse face 46 of beam 37. Electrical conductor 23 is located in groove 43 and retained therein when beams 37 and 38 are in their closed positions. Alternatively, conductor 23 can be positioned and retained in groove 39 during the insertion procedure. As shown in FIG. 6, opposite ends of groove 43 have enlarged portions or openings in lip 44 for accommodating the portion of lead 23 that enters and exits groove 43 as seen in FIG. 1. These openings prevent pinching and compression of lead 23. Groove 39 has similar openings in lip 41 for accommodating lead 23 when placed in groove 39.

Figure 9:
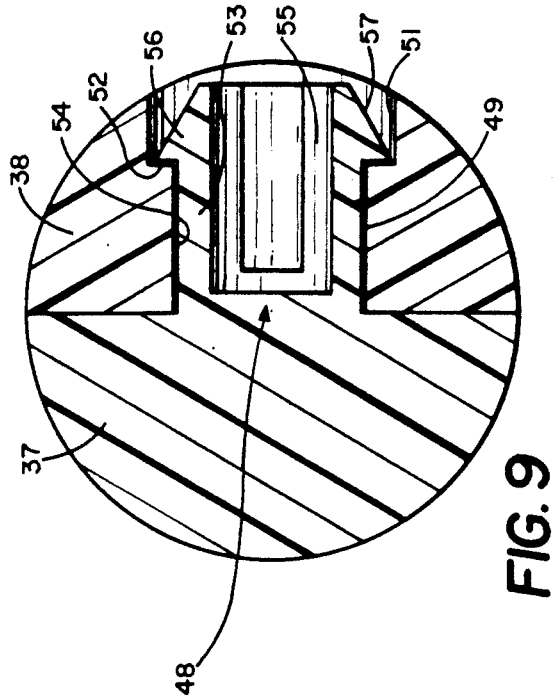
FIG. 9 is an enlarged sectional view taken along the line 9—9 of FIG. 6.

Pivot assemblies 47 and 48 are identical in structure. The following description is directed to pivot assembly 48 shown in detail in FIG. 9. Beam 38 has a transverse bore 49 having an enlarged outer recess 51. An annular shoulder 52 joins recess 51 with bore 49. Beam 37 has a transverse projection or split body 53 located in bore 49. Body 53 has outer cylindrical surfaces 54 that ride on the surface of bore 49 to form a bearing. Body 53 has a central split bore 55 that separates body 53 into four quarter circular parts. The outer end of body 53 has a split head 56 that extends outwardly from body 53 and engages shoulder 52 to retain beams 37 and 38 in pivotal assembled relation. Head 56 has a cone shaped outer surface 57 which allows body 53 to be moved through bore 49 and snapped into locking position with shoulder 52.

Figure 11:
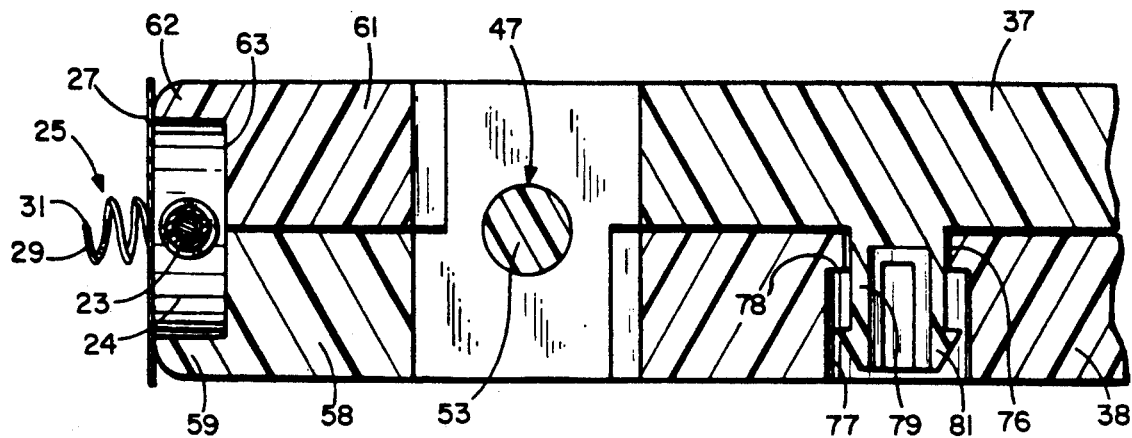
FIG. 11 is an enlarged sectional view taken along the line 11—11 of FIG. 1.

Referring to FIGS. 8 and 11, the distal end 58 of beam 37 has a first forwardly directed jaw 59 located opposite the distal end 61 of beam 38. A second jaw 62 on end 61 faces jaw 59. As shown in FIG. 8, jaws 59 and 62 have generally arcuate shapes and surround a generally circular pocket 63. Head 24 of the lead fits into pocket 63 as shown in FIG. 11.

Returning to FIG. 8, jaw 59 has a convex shape with opposite ends 64 and 66 that face opposite ends 67 and 68 of jaw 62. Adjacent ends 64, 67 and 66, 68 are circumferentially spaced from each other forming side openings 69 and 71. Openings 69 and 71 are in general longitudinal alignment with longitudinal grooves 39 and 43 in beams 37 and 38. In use side openings 69 and 71 selectively accommodate the portion of electrical conductor 23 that immediately projects from the side of body 24 and extends the length of tool 20, as shown in FIG. 1.

Figure 10:
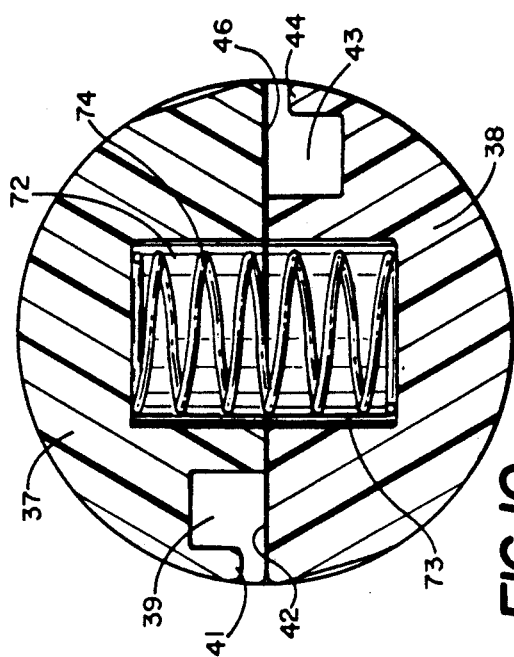
FIG. 10 is an enlarged sectional view taken along the line 10—10 of FIG. 6.
Figure 7:
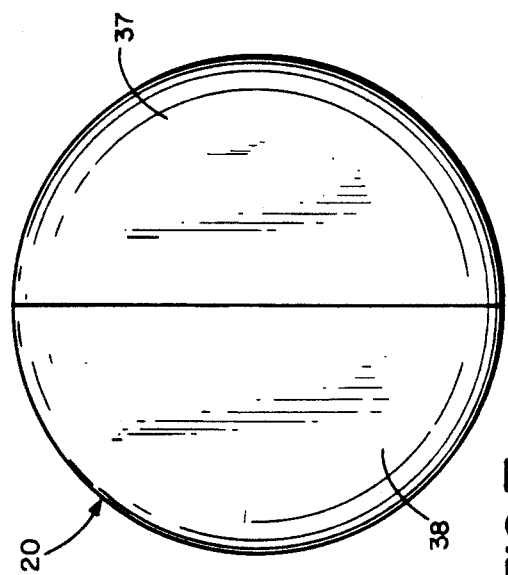
FIG. 7 is an enlarged end view of the proximal end of the introducer of FIG. 6.
Figure 16:
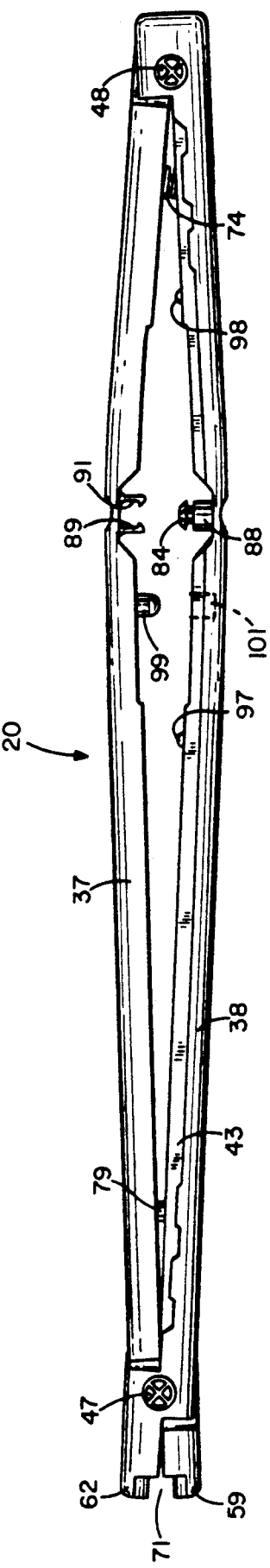
FIG. 16 is a side elevational view of the introducer in the open position.

Referring to FIG. 10, the proximal end of beams 37 and 38 have aligned bores 72 and 73 accommodating a coil spring 74. Spring 74 biases the beams to outward bowed positions, as shown in FIG. 16, thereby opening jaws 59 and 62. When jaws 59 and 62 are open they release the gripping force on head 24 of the lead so that tool 20 can be removed from the lead. Alternatively, the tool with the open jaws 59 and 62 can be positioned about head 24 to regrip the head 24 as hereinafter described.

As shown in FIG. 11, the distal end of beam 38 has a bore 76 leading to an enlarged recess 77 having an annular shoulder 78 separating the bottom of recess 77 from bore 76. A body or split projection 79 joined to beam 37 projects through bore 76 into recess 77. Body 79 has an enlarged cone shaped or tapered head 81 adapted to engage shoulder 78 to limit the outward movements of beams 37 and 38. Body 79 and bore 76 co-act with each other to guide relative movements between beams 37 and 38.

Figure 12:
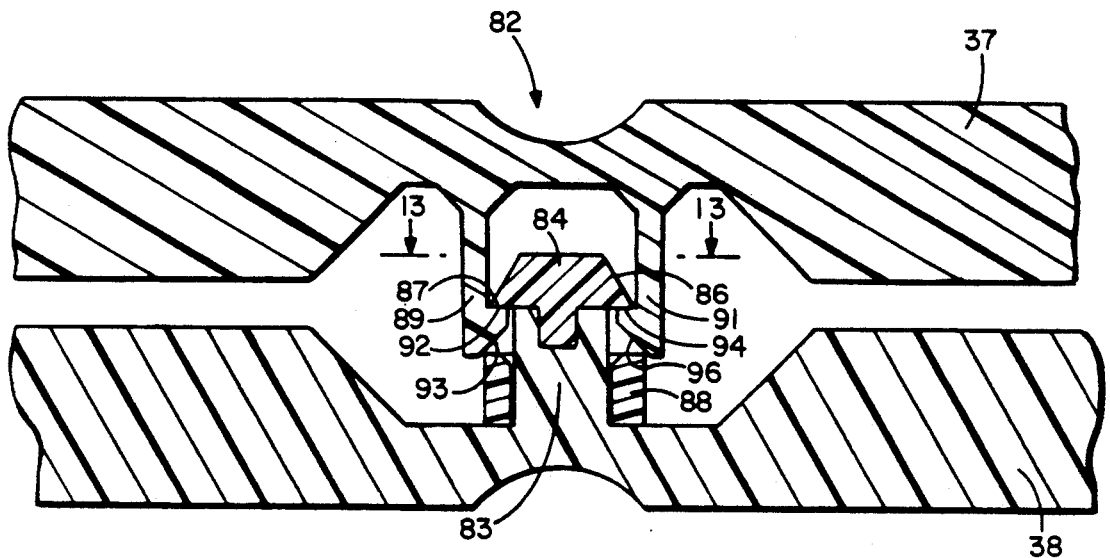
FIG. 12 is an enlarged sectional view taken along the line 12—12 of FIG. 1.

Beams 37 and 38 are retained in their closed or locked position with a releasable lock assembly indicated generally at 82. Referring to FIG. 12, lock assembly 82 is in the hold or lock position whereby beams 37 and 38 retain jaws 59 and 62 in firm gripping relation with the opposite outside portions of head 24 of pacing lead 21. Beam 38 has an upwardly directed cylindrical projection 83 which accommodates a head 84. Head 84 is sonic welded or otherwise permanently joined to the end of projection 83. Head 84 has upwardly and inwardly tapered side wall 86 and inwardly directed annular shoulder 87. A cylindrical sleeve 88 is slideably interposed about projection 83 between shoulder 87 and the inside wall of beam 38. Sleeve 88 has a length shorter than the distance between shoulder 87 and beam 38 whereby sleeve 88 is free to move between head 84 and beam 38.

Figure 13:
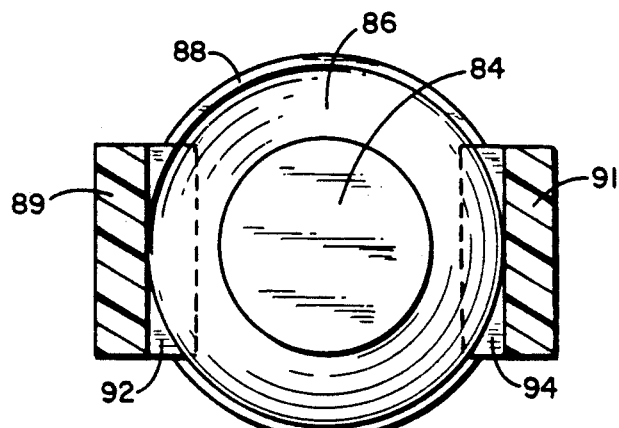
FIG. 13 is an enlarged sectional view taken along line 13—13 of FIG. 12.

As shown in FIG. 13, sleeve 88 has an outside diameter that is slightly larger than the outside diameter of head 84. A pair of downwardly directed flexible latch fingers 89 and 91 are joined to beam 37 and project downwardly adjacent opposite portions of head 84. Latch finger 89 has an inwardly directed shoulder or hook 92 and a downwardly and outwardly tapered face 93. Latch finger 91 has an inwardly directed shoulder or hook 94 and a downwardly and outwardly tapered face 96. Hooks 92 and 94 are in generally the same plane and engage opposite portions of shoulder 87 to hold beams 37 and 38 in their closed or locked positions. As shown in FIG. 13, shoulders 92 and 94 fit under diametrically opposite portions of head 84 above the outer circumferential surface of sleeve 88. As shown in FIGS. 6 and 16, beam 38 has a pair of ribs 97 and 98 on opposite sides of lock assembly 82 that function as fulcrums during the release of the lock assembly as hereinafter described. Beam 37 also has a guide pin 99 that fits into a hole or recess 101 in beam 38 to prevent relative lateral displacements of beams 37 and 38 and insure that lock assembly 82 remains locked.

Figure 14:
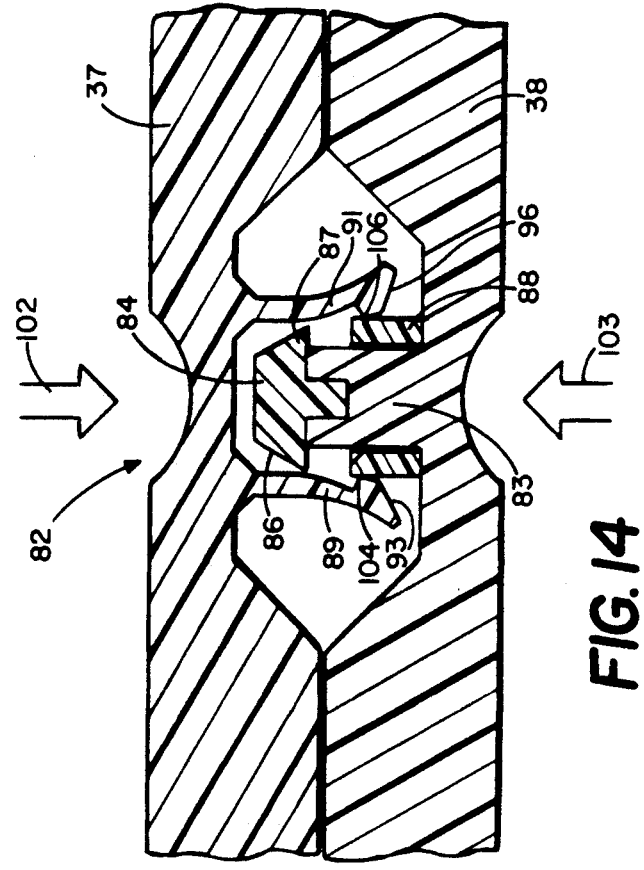
FIGS. 14 and 15 are sectional views similar to FIG. 12 showing the releasing of the lock assembly of the introducer.

Referring to FIG. 14, when lock assembly 82 is to be released opposite squeezing forces indicated by arrows 102 and 103 are applied to beams 37 and 38 on opposite sides of lock assembly 82. Beams 37 and 38 are biased together against the force of spring 74 until beam 37 engages ribs 97 and 98 on beam 38. An increased force on beams sections opposite lock assembly 82 causes these beam sections to fulcrum or pivot on ribs 97 and 98 and deflect inwardly or toward each other. Latch fingers 89 and 91 move downwardly from head 84 and onto sleeve 88. The linear edge 104 of latch finger 89 grips one side of sleeve 88. Simultaneously the linear edge 106 of latch finger 91 engages an opposite portion of sleeve 88. Latch fingers 89 and 91 are biased outwardly as they slide over the tapered side wall 86 of head 84 onto sleeve 88. When forces 102 and 103 are released from beams 37 and 38, as indicated by arrows 107 and 108 in FIG. 15, beams 37 and 38 will move away from each other to bowed or open positions as shown in FIG. 16, due to the biasing forces of beams 37 and 38 and spring 74. Latch fingers 89 and 91 will carry sleeve 88 up into engagement with shoulder 87 of head 84. The continued spreading apart of beams 37 and 38 carry latch fingers 89 and 91 over head 84 since the diameter of sleeve 88 is larger than the diameter of head 84. When beams 37 and 38 are in their open position, as shown in FIG. 16, latch fingers 89 and 91 are spaced from head 84. Jaws 59 and 62 are spread apart in their open position.

In use, introducer 20 is initially in the closed position as shown in FIG. 1. Head 24 of pacing lead 21 is located in the pocket 63 with conductor 23 projecting from side opening 71. The electrical conductor 23 is located in groove 43 and retained therein by lip 44. The helical electrode 25 projects in a forward direction so that it can be screwed into the heart tissue by rotating introducer 20. Alternatively, the electrical conductor 23 can be located in groove 39 with the end of the conductor joined to the head 24 passing through side opening 69. Beams 37 and 38 are held together by flexible latch fingers 89 and 91 fitting over head 84 whereby shoulders 92 and 94 engage shoulder 87 of head to hold beams 37 and 38 in their locked closed positions. The jaws 59 and 62 firmly grip opposite sides of head 24.

Figure 15:
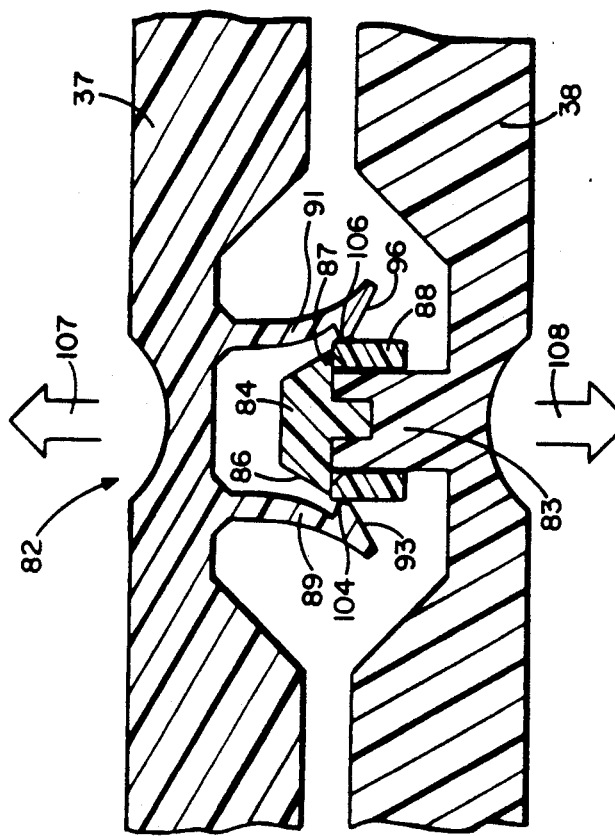

Introducer 20 permits a quick one handed release of the entire lead after attachment. This is accomplished by using one hand applying a squeezing force to beams 37 and 38 on opposite sides of the lock assembly 82 as shown in FIG. 14. When the force is released, as shown in FIG. 15, lock assembly 82 will automatically disengage without the assistance of the other hand of the user or another person. The one handed operation can be used to also grip head 24 so that the lead can be removed from the myocardium and repositioned.

During the implant procedure the pointed end 31 of the electrode 25 is placed against the heart tissue and introducer 20 is rotated as indicated by the curved arrow 109 in FIG. 1. As introducer 20 is rotated, helical electrode 25 is firmly screwed into the heart tissue or myocardium until netting 27 firmly contacts the outer surface of the tissue. Netting 27 provides a secure and permanent placement of electrode 25 in the tissue in that the netting promotes rapid fibrosis in and around the netting as well as around the head 24. The platinum black particles 29 are in continuous intimate contact with the heart tissue throughout the helical length of the exterior section of electrode 25 which results in decreased electrical losses at the electrode-tissue interface, increased current density to the heart tissue, uniform current density lowering stimulation thresholds and increasing intracardiac electrical signal amplitudes.

Introducer 20 is released from head 24 without further rotation or axial movement. No forces are exerted on head 24 to release the clamping of jaws 59 and 62 from head 24. The introducer 20 can be axially withdrawn from head 24 after jaws 59 and 62 have been released. This is accomplished by a mere squeezing and releasing action on beams 37 and 38 on opposite sides of lock assembly 82 as illustrated in FIGS. 14 and 15.

The invention has been described with particular reference to a perferred embodiment thereof, but it will be understood that variations and modifications can be made by one skilled in the art without departing from the invention.

We claim:

1. A releasable lock assembly for selectively connecting and releasing first and second members comprising: a pair of flexible fingers secured to the first member, each finger having a hook, holding means secured to the second member engageable with the finger means to hold the first and second members adjacent each other, said holding means including a head engageable with the hooks to hold the first and second members adjacent each other, and means to release the finger means from the holding means on movement of the first and second members toward each other thereby allowing the first and second members to move away from each other, said means to release the finger means being operable to release the hooks from the head when the first and second members are moved toward each other.

2. The lock assembly of claim 1 wherein: the means to release the finger means includes sleeve means surrounding the holding means adapted to engage the finger means to release the hooks from said head on movement of the fingers onto said sleeve means whereby the first and second members move away from each other.

3. The lock assembly of claim 2 wherein: said head includes a shoulder engageable with the hooks to hold the first and second members adjacent each other, said sleeve means surrounding the holding means being spaced from said shoulder to allow the hooks to engage the shoulder, said hooks being movable onto the sleeve means to disengage the hooks from the shoulder when the first and second members are moved toward each other to allow the first and second members to move away from each other.

4. The lock assembly of claim 3 wherein: said shoulder has a diameter, and said sleeve means has an outside diameter larger than the diameter of the shoulder whereby the sleeve means allows the hooks to clear the shoulder to release the lock assembly.

5. A releasable lock assembly for selectively connecting and releasing first and second members comprising: finger means secured to the first member, holding means secured to the second member engageable with the finger means to hold the first and second members adjacent each other, and means to release the finger means from the holding means on movement of the first and second members toward each other thereby allowing the first and second members to move away from each other, said holding means includes a projection member secured to the second member, a head mounted on said projection member, said finger means having hook means engageable with said head to hold the first and second members adjacent each other, and sleeve means surrounding said projection member adapted to be engaged by said finger means to release the hook means from said head on movement of the finger means onto said sleeve means whereby the first and second members move away from each other.

6. The lock assembly of claim 5 wherein: the finger means has a pair of flexible fingers having hooks, said head having a shoulder engagable with the hooks to hold the first and second members adjacent each other, said sleeve means being spaced from said shoulder to allow the hooks to engage the shoulder, said hooks being movable onto the sleeve means to disengage the hooks from the shoulder when the first and second members are moved toward each other to allow the first and second members to move away from each other.

7. The lock assembly of claim 6 wherein: said shoulder has a diameter, and said sleeve means has an outside diameter larger than the diameter of the shoulder whereby the sleeve means allows the hooks to clear the shoulder to release the lock assembly.

8. The hook assembly of claim 5 wherein: said head has a shoulder engageable with the hook means to hold the first and second members adjacent each other, said sleeve means being spaced from said shoulder to allow the hook means to engage the shoulder, said hook means being movable onto the sleeve means to disengage the hook means from the shoulder when the first and second members are moved toward each other to allow the first and second members to move away from each other.

9. The lock assembly of claim 8 wherein: said shoulder has a diameter, and said sleeve means has an outside diameter larger than the diameter of the shoulder whereby the sleeve means allows the hook means to clear the shoulder to release the lock assembly.

* * * * *